(12) United States Patent
Feng et al.

(10) Patent No.: US 11,915,417 B2
(45) Date of Patent: Feb. 27, 2024

(54) SYSTEMS, METHODS, AND APPARATUSES FOR TRAINING A DEEP MODEL TO LEARN CONTRASTIVE REPRESENTATIONS EMBEDDED WITHIN PART-WHOLE SEMANTICS VIA A SELF-SUPERVISED LEARNING FRAMEWORK

(71) Applicant: Arizona Board of Regents on Behalf of Arizona State University, Scottsdale, AZ (US)

(72) Inventors: Ruibin Feng, Scottsdale, AZ (US); Zongwei Zhou, Tempe, AZ (US); Jianming Liang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 429 days.

(21) Appl. No.: 17/240,271

(22) Filed: Apr. 26, 2021

(65) Prior Publication Data
US 2021/0342646 A1 Nov. 4, 2021

Related U.S. Application Data

(60) Provisional application No. 63/018,345, filed on Apr. 30, 2020.

(51) Int. Cl.
*G06T 7/00* (2017.01)
*G06T 15/08* (2011.01)
(Continued)

(52) U.S. Cl.
CPC ........ *G06T 7/0012* (2013.01); *G06F 18/2155* (2023.01); *G06T 7/174* (2017.01);
(Continued)

(58) Field of Classification Search
CPC ....... G06T 7/0012; G06T 7/174; G06T 15/08; G06T 17/10; G06T 2207/20081;
(Continued)

(56) References Cited

U.S. PATENT DOCUMENTS 11,354,778 B2 * 6/2022 Chen ...................... G06T 5/002

OTHER PUBLICATIONS

Bohdan Petryshak, "Medical image segmentation using shape prior information and deep neural networks", 2019, Ukrainian Catholic University, pp. 16-17, 20, 23, and 28. (Year: 2019).*
(Continued)

*Primary Examiner* — Emily C Terrell
*Assistant Examiner* — Stefano Anthony Dardano
(74) *Attorney, Agent, or Firm* — Elliott, Ostrander & Preston, P.C.

(57) ABSTRACT

Described herein are means for training a deep model to learn contrastive representations embedded within part-whole semantics via a self-supervised learning framework, in which the trained deep models are then utilized for the processing of medical imaging. For instance, an exemplary system is specifically configured for performing a random cropping operation to crop a 3D cube from each of a plurality of medical images received at the system as input; performing a resize operation of the cropped 3D cubes; performing an image reconstruction operation of the resized and cropped 3D cubes to predict the resized whole image represented by the original medical images received; and generating a reconstructed image which is analyzed for reconstruction loss against the original image representing a known ground truth image to the reconstruction loss function. Other related embodiments are disclosed.

20 Claims, 11 Drawing Sheets

(51) Int. Cl.
  *G06T 17/10* (2006.01)
  *G06T 7/174* (2017.01)
  *G06F 18/214* (2023.01)
  *G06V 10/82* (2022.01)
(52) U.S. Cl.
  CPC .............. *G06T 15/08* (2013.01); *G06T 17/10* (2013.01); *G06V 10/82* (2022.01); *G06T 2207/20081* (2013.01); *G06T 2207/20084* (2013.01); *G06T 2207/20132* (2013.01); *G06T 2207/30016* (2013.01); *G06T 2207/30056* (2013.01); *G06V 2201/031* (2022.01)
(58) Field of Classification Search
  CPC . G06T 2207/20084; G06T 2207/20132; G06T 2207/30016; G06T 2207/30056; G06T 2207/30064; G06T 2207/30096; G06T 7/11; G06F 18/2155; G06V 10/82; G06V 2201/031; G06V 2201/03; G06N 3/045; G06N 3/08; G16H 30/40; G16H 50/20
  See application file for complete search history.

(56) References Cited

OTHER PUBLICATIONS

Ning Zhang, "Detecting Very Small and Sparse Lesions in Medical Images", Feb. 2020, University of Massachusetts Lowell, p. 16 (Year: 2020).*
Xinze Chen, Guangliang Cheng, Yinghao Cai, Dayong Wen, and Heping Li, "Semantic Segmentation with Modified Deep Residual Networks", 2016, Springer Nature Singapore Pte Ltd, pp. 42-54. (Year: 2016).*
Pruijssers, M. H. C. W. End-to-end Semantic Segmentation of Roads in Satellite Imagery. Diss. Tilburg University, 2019. (Year: 2019).*
Bahl, Gaetan, et al. "Low-power neural networks for semantic segmentation of satellite images." Proceedings of the IEEE/CVF International Conference on Computer Vision Workshops. 2019. (Year: 2019).*
Cuadrado Conde, Cristian. Fish detection in coastal areas. MS thesis. Universitat Politècnica de Catalunya, 2020. (Year: 2020).*
Ardila, D. et al., "End-to-end lung cancer screening with three-dimensional deep learning on low-dose chest computed tomography," Nature Medicine, 25(6), 2019, pp. 954-961.
Armato III, S.G. et al., "The lung image database consortium (LIDC) and image database resource initiative (IDRI): a completed reference database of lung nodules on CT scans," Medical physics 38(2), 2011, pp. 915-931.
Bachman, P. et al., "Learning representations by maximizing mutual information across views," Advances in Neural Information Processing Systems, 32, 2019, 11 pages.
Bakas, S. et al., "Identifying the best machine learning algorithms for brain tumor segmentation, progression assessment, and overall survival prediction in the BRATS challenge,". arXiv preprint arXiv:1811.02629, 2018, 49 pages.
Bilic, P. et al., "The liver tumor segmentation benchmark (lits)," arXiv preprint arXiv:1901.04056, 2019, 24 pages.
Bishop, C.M. et al., "Neural networks for pattern recognition," 1995, Oxford University Press.
Carreira, J. et al., "Quo vadis, action recognition? a new model and the kinetics dataset," Proceedings of the IEEE Conference on Computer Vision and Pattern Recognition, 2017, pp. 6299-6308.
Chen, S. et al., "Med3d: Transfer learning for 3d medical image analysis," arXiv preprint arXiv: 1904.00625, 2019, 12 pages.
Chen, T. et al., "A simple framework for contrastive learning of visual representations," arXiv preprint arXiv:2002.05709, 2020, 11 pages.
Dosovitskiy, A. et al., "Discriminative unsupervised feature learning with convolutional neural networks," Advances in neural information processing systems, 2014, 9 pages.
Gibson, E. et al., "Niftynet: a deep-learning platform for medical imaging," Computer methods and programs in biomedicine, 2018, 158:113-122.
He, K. et al., "Momentum contrast for unsupervised visual representation learning," arXiv preprint arXiv:1911.05722, 2020, 10 pages.
Misra, I. et al., "Self-supervised learning of pretext-invariant representations," arXiv preprint arXiv:1912.01991, 2020, 11 pages.
Noroozi, M. et al., "Unsupervised learning of visual representations by solving jigsaw puzzles," European Conference on Computer Vision, 2016, pp. 69-84, Cham: Springer International Publishing,.
Rajpurkar, P. et al., "Chexnet: Radiologist-level pneumonia detection on chest x-rays with deep learning," arXiv preprint arXiv:1711.05225, 2017, 7 pages.
Ronneberger, O. et al., "U-net: Convolutional networks for biomedical image segmentation, "Medical Image Computing and Computer-Assisted Intervention—MICCAI 2015: 18th International Conference, Munich, Germany, Oct. 5-9, 2015, Proceedings, Part III 18, pp. 234-241, Springer International Publishing.
Setio, A.A.A. et al., "Validation, comparison, and combination of algorithms for automatic detection of pulmonary nodules in computed tomography images: the Luna16 challenge," Medical image analysis 2017, 42, pp. 1-13.
Tajbakhsh, N. et al., "Computer-aided pulmonary embolism detection using a novel vessel-aligned multi-planar image representation and convolutional neural networks," Medical Image Computing and Computer-Assisted Intervention—MICCAI 2015: 18th International Conference, Munich, Germany, Oct. 5-9, 2015, Proceedings, Part II 18, 9 pages, Springer International Publishing.
Tian, Y. et al., "Contrastive multiview coding," arXiv preprint arXiv: 1906.05849, 2020, 16 pages.
Wang, X. et al., "Chestx-ray8: Hospital-scale chest x-ray database and benchmarks on weakly-supervised classification and localization of common thorax diseases," Proceedings of the IEEE conference on computer vision and pattern recognition, 2017. pp. 2097-2106.
Wu, Z. et al., "Unsupervised feature learning via non-parametric instance discrimination," Proceedings of the IEEE Conference on Computer Vision and Pattern Recognition, 2018, pp. 3733-3742.
Ye, M. et al., "Unsupervised embedding learning via invariant and spreading instance feature," Proceedings of the IEEE /CVF Conference on Computer Vision and Pattern Recognition, 2019, pp. 6210-6219.
Zhang, R. et al., Colorful image colorization Computer Vision-ECCV 2016: 14th European Conference, Amsterdam, The Netherlands, Oct. 11-14, 2016, Proceedings, Part III 14 2016, pp. 649-666, Springer International Publishing.
Zhou, Z. et al., "Models genesis: Generic autodidactic models for 3d medical image analysis," Medical Image Computing and Computer Assisted Intervention—MICCAI 2019: 22nd International Conference, Shenzhen, China, Oct. 13-17, 2019, Proceedings, Part IV 22 2019, pp. 384-393, Springer International Publishing.

* cited by examiner

Table 1 - 199

| Approach 101 | NCC 102<br>AUC % 107 | NCS 103<br>IoU % 108 | LCS 104<br>IoU % 108 | ECC 105<br>AUC % 107 | BMS 106<br>IoU % 108 |
|---|---|---|---|---|---|
| Scratch 109 | 94.25±5.07 | 74.05±1.97 | 77.82±3.87 | 79.99±8.06 | 63.91±1.41 |
| I3D 110 | 98.26±0.27 | 71.58±0.55 | 70.65±4.26 | 80.55±1.11 | 67.83±0.75 |
| NiftyNet 111 | 94.14±4.57 | 52.98±2.05 | 83.23±1.05 | 77.33±8.05 | 60.78±1.00 |
| MedicalNet 112 | 95.80±0.49 | 75.68±0.32 | 85.52±0.58 | 86.43±1.44 | 66.09±1.35 |
| Models Genesis 113 | 97.90±0.57 | 77.62±0.64 | 84.17±1.93 | 87.20±2.87 | 68.08±1.05 |
| Parts2Whole 114 | 98.67±0.23 | 75.86±0.61 | 86.70±0.62 | 84.11±2.14 | 68.33±0.41 |
| *p*-value 115 | 0.0011 | 0.1700 | 0.0002 | 0.2126 | 0.2654 |

Best Approaches 116

Equivalent Performance 117

FIG. 1B

Table 2 - 299

| Setting 251 | [1/16, 1] w/ s.c. 252 | [1/16, 1] 253 | [1/16, 1/2] 254 | [1/16, 1/4] 255 | [1/16, 1/8] 256 | [1/32, 1/16] 257 |
|---|---|---|---|---|---|---|
| NCC 258 | 88.48±8.24 | 93.78±2.12 | 91.48±0.45 | 94.84±1.58 | 93.52±1.32 | 91.69±4.12 |
| NCS 259 | 70.64±0.21 | 72.72±0.42 | 73.29±0.58 | 74.23±0.87 | 73.43±0.32 | 73.66±0.36 |

Pre-trained encoder and decoder fine-tuned on target task 260

Plateau 261

FIG. 2B

Table 3 - 699

| Traget Task | NCC | | NCS | |
|---|---|---|---|---|
| Training set size | 5,000 | 28,144 | 5,000 | 28,144 |
| Parts2Whole | 94.84±1.66 | 97.08±0.53 | 74.21±0.27 | 74.44±0.34 |
| InsDisc | 91.00±2.45 | Infeasible | 73.59±0.37 | Infeasible |

FIG. 6B

SYSTEMS, METHODS, AND APPARATUSES FOR TRAINING A DEEP MODEL TO LEARN CONTRASTIVE REPRESENTATIONS EMBEDDED WITHIN PART-WHOLE SEMANTICS VIA A SELF-SUPERVISED LEARNING FRAMEWORK

CLAIM OF PRIORITY

This non-provisional U.S. Utility patent application is related to, and claims priority to, the U.S. provisional patent application Ser. No. 63/018,345, filed Apr. 30, 2020, entitled "SYSTEMS, METHODS, AND APPARATUSES FOR TRAINING A DEEP MODEL TO LEARN CONTRASTIVE REPRESENTATIONS EMBEDDED WITHIN PART-WHOLE SEMANTICS VIA A SELF-SUPERVISED LEARNING FRAMEWORK," the entire contents of which are incorporated herein by reference.

GOVERNMENT RIGHTS AND GOVERNMENT AGENCY SUPPORT NOTICE

This invention was made with government support under ROT H1,128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL HELD

Embodiments of the invention relate generally to the field of medical imaging and analysis using convolutional neural networks for the classification and segmentation of medical images, and more particularly, to systems, methods, and apparatuses for raining a deep model to learn contrastive representations embedded within part-whole semantics via a self-supervised learning framework, in which the trained deep models are then utilized for the processing of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Not only is annotating medical images tedious and time-consuming, but it also demands costly, specialty-oriented expertise, which is not easily accessible.

Contrastive representation learning achieves the new state of the art in computer vision, but requires huge mini-batch sizes, special network design, or memory banks, making it impractical for 3D medical imaging applications.

To address this challenge, a self-supervised learning framework is newly introduced herein and described in greater detail below, which is configured to build contrastive representations within an image reconstruction framework, effectively addressing the aforementioned barriers to 3D contrastive learning.

The newly introduced self-supervised learning framework as introduced herein may be referred to as a "Parts2Whole" or "Parts2Whole framework," as the methodology directly exploits the universal and intrinsic part-whole relationship. The Parts2Whole framework has been extensively evaluated on five distinct medical tasks and compared four competing publicly available 3D pre-trained models. The experimental results demonstrate that the Part2Whole framework as described herein significantly outperforms in two out of five tasks while achieves competitive performance on the rest three. Further empirical analysis detailed below further suggests that such superior performance is attributed to the contrastive representations learned within the newly described Parts2Whole framework.

Medical images are naturally associated with rich semantics about the human anatomy, reflected in an abundance of recurring anatomical patterns, offering the unique potential to foster deep semantic representation learning and yield semantically more powerful models for different medical applications. But conventional methodologies have been relegated to the 2D space given the complexity and computational barriers to processing 3D medical imagery.

How exactly such strong yet free semantics embedded in medical images can be harnessed for self-supervised learning remains largely unexplored. To this end, self-supervised learning framework described, as implemented via the Parts2Whole framework overcomes these barriers and thus brings greater efficiency and computational feasibility to processing 3D medical images that heretofore was not practical.

Problematically, annotating medical imaging is tedious and time-consuming, and demands costly, specialty-oriented knowledge and skills, which are not easily accessible. Furthermore, any misdiagnosis from failure to recognize or correctly identify anatomical structures and abnormalities may result in potentially devastating impacts on patient morbidity and mortality.

The described embodiments therefore provide enhanced solutions to improve upon conventionally known medical image processing and learning techniques by leveraging contrastive representation learning via the self-supervised learning framework in which a deep model is trained to reconstruct a whole from its parts, thus compelling the deep model to learn contrastive representations embedded with part-whole semantics.

The present state of the art may therefore benefit from the systems, methods, and apparatuses for training a deep model to learn contrastive representations embedded within part-whole semantics via a self-supervised learning framework, as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 1B depicts Table 1 describing results demonstrating that the pre-trained model achieves significantly better or at least comparable performance on five distinct medical target tasks over four publicly available 3D models pre-trained in both a supervised and a self-supervised fashion, in accordance with disclosed embodiments;

FIG. 2B depicts Table 2 describing the target task performance on source models pre-trained on different proxy task settings, in accordance with disclosed embodiments;

FIG. 6B depicts Table 3 describing how the Parts2Whole framework makes contrastive representation learning feasible for 3D medical imaging, in accordance with disclosed embodiments.

DETAILED DESCRIPTION

Figure 1A:
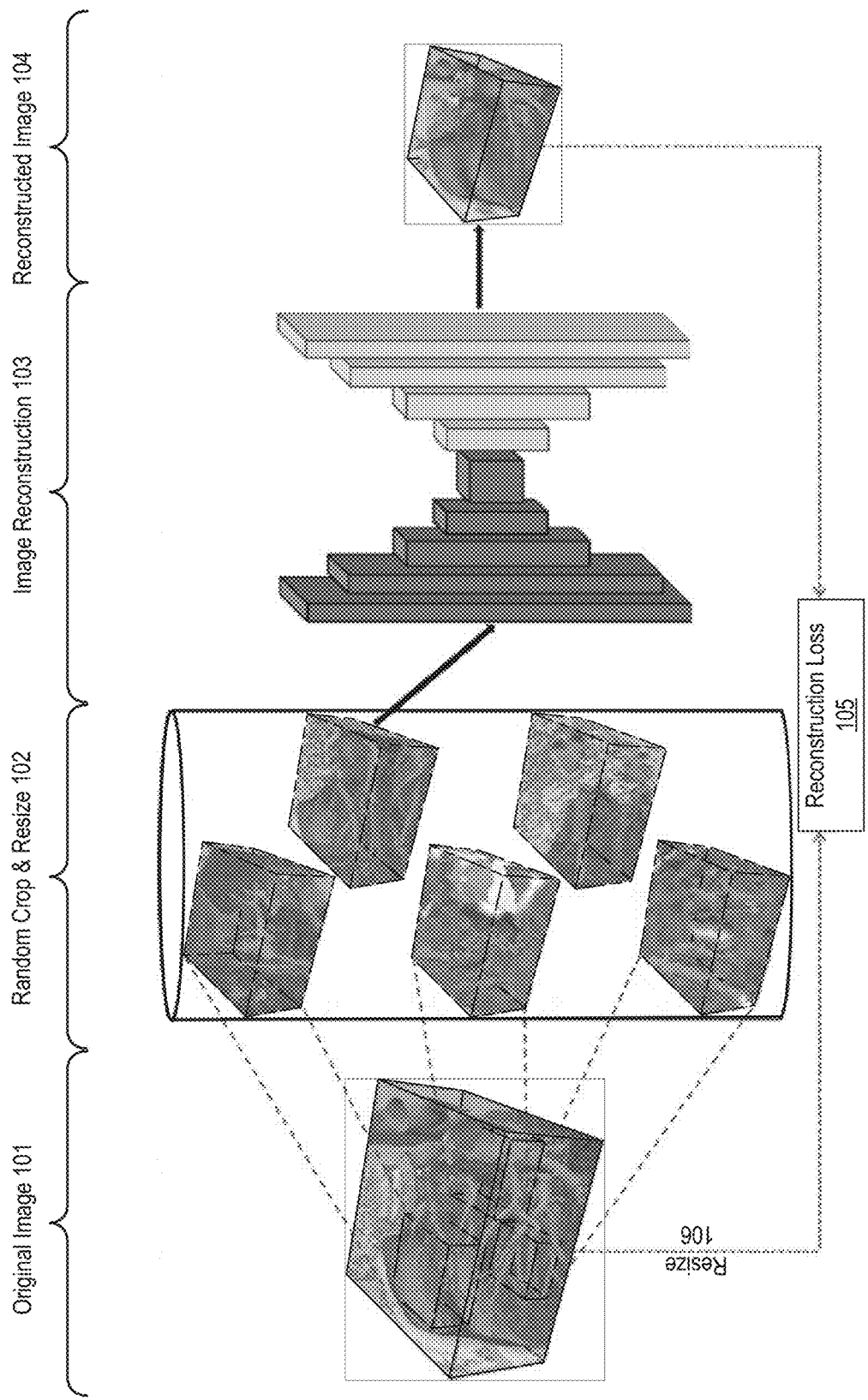
FIG. 1A depicts the use of the disclosed self-supervised learning framework for reconstructing a resized whole portion cropped and resized from its resized randomly cropped parts, in accordance with disclosed embodiments.

Described herein are systems, methods, and apparatuses for training a deep model to learn contrastive representations embedded within part-whole semantics via a self-supervised learning framework, in which the trained deep models are then utilized in the context of medical imaging.

Contrastive representation learning has made a leap in computer vision. For example, Techniques such as InsDisc, CMC, and PIRL utilize contrastive losses to significantly boost the performance of Exemplar, Colorization, and Jig-Saw, based image processing, respectively.

The MoCo technique introduces the momentum mechanism, and the SimCLR technique proposes a simple framework for contrastive learning, with both methods achieving state-of-the-art results and even outperforming supervised ImageNet pre-training.

However, contrastive learning requires huge mini-batch sizes, special network design, or a memory bank to store feature representations of all images in the dataset, making contrastive learning techniques impractical for 3D medical imaging applications.

Taking the mini-batch size as an example, the SimCLR technique recommends 4096 mini-batch sizes, Which is infeasible for 3D image data due to practical limitations GPU memory.

Embodiments described herein present solutions which overcome shortcomings with previously known techniques and make contrastive representation learning feasible and efficient for 3D medical imaging. For example, according to certain embodiments, contrastive representations are learned via an image reconstruction framework, leveraging recent advances in 3D representation learning, so as to effectively address the aforementioned barriers associated with contrastive learning in the context 3D medical image processing.

According to a particular embodiment, the described framework exploits a universal and intrinsic property known as the part-whole relationship, in which an entire image is regarded as the whole and any of its patches are considered as its parts.

By reconstructing a whole from its parts, the described framework trains a deep model which is compelled to learn contrastive representations embedded with part-whole semantics. That is to say, the deep model consequently learns (1) the representations of parts belonging to the same whole are close, and additionally learns (2) the representations of parts belonging to different wholes that are far away.

Specifically described embodiments implement a self-supervised learning framework which may be referred to as a Parts2Whole framework. While the described Parts2Whole framework may reconstruct the surrounding contents of a given patch similar to prior known techniques which utilize, for example, out-painting, the described Parts2Whole framework is differentiated in that the deep models trained via the framework learn contrastive representations enriched by part-whole semantics which yields better transferability than prior known techniques.

An exemplary pre-trained model provided by the Parts2Whole framework has been extensively evaluated on five distinct medical target tasks and compared with four competing publicly available 3D models pre-trained in either a fully supervised or a self-supervised fashion.

The statistical analysis provided below at Table 1 (refer to FIG. 1B) demonstrates that the disclosed Parts2Whole framework significantly outperforms prior known techniques in two out of five tasks while achieving competitive performance on the other three, thus providing competitive or significantly better results over all prior known models that were tested.

Furthermore, the Parts2Whole framework was empirically validated and demonstrably shown to be capable of learning contrastive representations within an image reconstruction framework. As will be discussed in greater detail below, the Parts2Whole framework and design is justified by ablating its main components as demonstrated by the results at Table 2 (refer to FIG. 2B). Further discussed is the capability of utilizing the Parts2Whole framework and design for 2D applications.

FIG. 1A depicts the use of the disclosed self-supervised learning framework for reconstructing a resized whole portion cropped and resized from its resized randomly cropped parts.

As shown here, the new self-supervised learning framework, called Parts2Whole, exploits a universal and intrinsic property, known as the part-whole relationship, in which an entire image is regarded as the whole and any of its patches are considered as its parts. The Parts2Whole framework described herein learns contrastive representations from the original image 101 that are embedded within the part-whole semantics by reconstructing a resized whole portion of the original image 101 (left-most image) from its resized randomly cropped parts 102 (depicted left of center).

So as to avoid trivial solutions, each whole is cropped utilizing random scales and random aspect ratios which thus erase low-level cues across different parts while maintaining informative structures and textures.

Further still, according to certain embodiments, skip connections are intentionally not utilized within the Convolutional Neural Network (CNN) so as to avoid low-level details passing from the encoder to the decoder of the CNN, thus yielding generic pre-trained models (e.g., trained deep models) with strong transferability. According to such embodiments, the model is trained in an end-to-end fashion and the reconstruction loss is measured with Euclidean distance.

For example, according to a particular embodiment, the self-supervised learning framework learns contrastive representations embedded with part-whole semantics by reconstructing the whole image from its parts, specifically utilizing unlabeled 3D images, specifically having no human or manual annotation whatsoever. The proposed self-supervised learning framework as illustrated at FIG. 1A thus takes an original 3D image 101 (left most image), then performs random cropping and resizing 102 (left of center image), followed by image reconstruction 103 (right of center image), and lastly generates a reconstructed image 104 (right most image) which is then analyzed for reconstruction loss 105 against the original image 101 representing a known ground truth image to the reconstruction loss function.

Problem formulation: According to a particular embodiment, processing denotes a set of 3D unlabeled images as $\{x_i \in X : i \in [1, N]\}$, where N is the number of whole images. Each image $x_i$ is random copped and resized 102 to generate various parts, referred to as $\{p_i^j \in P_i : i \in [1, N], j \in [1, M]\}$.

The task is to predict the (resized 106) whole image $x_i$ from its local patch $p_i^j$ by training a pair of encoder ($F_E$) and decoder ($F_D$) to minimize the loss function, denoted by $L = \Sigma_i \Sigma_j l (F_D (F_E (p_i^j)), R(x_i))$, where $R(\bullet)$ is a resize 106 function and $l(\bullet)$ is a metric measuring the difference between the output and target image. Euclidean distance is used as $l(\bullet)$ according to such an embodiment. Since the output images are generated via a shared decoder ($F_D$), the encoder ($F_E$) is forced to learn contrastive representations that embed the part-whole semantics. More particularly, after training, each of $F_E(p_i^j)$ and $F_E(p_i^{j'})$ are as close as possible if i=i' (e.g., if the two parts belong to the same whole image), whereas if i is not equal to i' then each of $F_E(p_i^j)$ and $F_E(p_i^{j'})$ are far away from each other as possible (e.g., two parts belong to different whole images). For such an embodiment, it is further assumed that no part is also a whole, so as to avoid ambiguous cases.

Removing skip connection: The skip connection (or the shortcut connection) which is utilized to connect the encoder and decoder in the U-Net architecture, is purposefully avoided according to certain embodiments. Use of a skip connection, allows the decoder to access the low-level features produced by the encoder layers such that the boundaries in segmentation maps produced by the decoder are ensured to be accurate.

However, if the network can solve the proxy task using lower-level patterns, then the network does not need to learn the semantically meaningful content. Therefore, in proxy task training as described herein, a modified 3D U-Net architecture is utilized in which the skip connection is intentionally removed and absent during training so as to force the bottleneck representations encoding high-level information. A pre-trained decoder is therefore not provided due to the lack of skip connection, thus differentiating the described embodiments from prior known techniques. Nonetheless, the described model offers very competitive performance on three segmentation tasks with a randomly initialized decoder, suggesting the pre-trained encoder learns strong, generic features.

Extracting local yet informative parts: The part size is a configurable feature component of the disclosed proxy task design in accordance with described embodiments. For example, when the cropping scale is too large, the task is downgraded to training an auto-encoder without learning semantics. Conversely, the cropping scale is too small, the task may be unsolvable as the parts that are too small simply do not contain enough information. To avoid such degenerate solutions, described embodiments may be restricted to cropped patches covering less than ¼ of the area of the whole image. By doing so, the low-level cues across different parts are largely erased. Additionally, certain embodiments set each part covering more than 1⁄16 of the area of the original image to have discriminative structures and textures, thus producing the generated parts as illustrated in at FIG. 1A (refer to the random crop and resize 102 left of center).

Experiments and Experiment Settings for Proxy Task Training: The described model was pre-trained on the LUNA-2016 dataset purposefully without using any label provided by the dataset. To avoid test data leakage, 623 CT scans were used instead of all 888 scans. First, original CT scans were cropped into small, non-overlapped 28,144 sub-scans with dimensions equal to 128×128×64. Each generated sub-scan was treated as a whole for the experiment and parts were cropped from it on the fly, resulting in the cropped parts containing [1⁄16, ¼] volume of the whole image.

Target Task Training: The pre-trained 3D model was then extensively evaluated by investigating five distinct medical applications, including lung nodule false positive reduction (NCC) 102, lung nodule segmentation (NCS) 103, liver segmentation (LCS) 104, pulmonary embolism false positive reduction (ECC) 105, and brain tumor segmentation (BMS) 106.

The Parts2Whole framework yields are competitive to 3D pre-trained models: The Parts2Whole framework was evaluated four publicly available 3D models, each pre-trained in both a supervised and a self-supervised fashion. Specifically, two of the models tested were supervised pre-trained on 3D medical segmentation tasks: NiftyNet 111 with Dense V-Networks and MedicalNet 112 with ResNet-101 as the backbone. The former was pre-trained with a multi-organ CT segmentation task, and the latter was pre-trained with an aggregate dataset (e.g., the 3DSeg-8) derived from eight public medical datasets. Further evaluated was I3D 110, which was pre-trained with natural videos but has been successfully applied for lung cancer classification.

FIG. 1B depicts Table 1 at element 199 describing results demonstrating that the pre-trained model achieves significantly better or at least comparable performance on five distinct medical target tasks over four publicly available 3D models pre-trained in both a supervised and a self-supervised fashion.

Each experiment was conducted for 10 trials and summarized with the mean and standard deviation (mean±s.t.d.). The paired t-test results between the methodology as described herein by approach 101, with the previous top solutions being tabulated in terms of their respective p-value 115. The best approaches 116 are bolded while the others are highlighted in gray if they achieved equivalent performance 117 compared with the best approach (e.g., $p>0.05$).

In the table above, the "p-values" 115 are calculated between the described Parts2Whole 114 framework and the previous top known solution, listed by approach 101 in the left most column (e.g., from the top row to bottom including methodologies from scratch 109, I3D 110, NiftyNet 111, MedicalNet 112, Models Genesis 113, and Parts2Whole 114 as described herein). The IOU 108 score was calculated using binarized masks with a threshold equal to 0.5 to better presented the segmentation quality, while uses the original masks without thresholding. The results shown here are different from those publicly reported because real data was utilized while Models Genesis 113 were evaluated with synthetic data.

For self-supervised learning, state of the art pre-trained Models Genesis 113 for 3D medical imaging were utilized as a baseline. The experimental results are summarized at Table 1 (refer to FIG. 1B), from which it may be observed that I3D works well on NCC 102 but performs inferiorly on the other four tasks, NCS 103, LCS 104, ECC 105, and BMS 106. This sub-optimal performance may be attributable to the marked difference between natural and medical domains. On the other hand, NiftyNet 111 and MedicalNet 112, which are fully supervised with medical data, also show relatively poor transferability according to the results. The main reason likely is due to the limited amount of annotation for supervising for those methodologies.

A piece of evidence is that MedicalNet 112 considerably outperforms NiftyNet 111 by aggregating eight datasets for pre-training. These observations highlight the significance of self-supervised learning in the 3D medical domain, which can close the domain gap and utilize the vast amount of un-annotated data. In contrast with fully supervised pre-training, both self-supervised learning methods (e.g., both Models Genesis 113 and the disclosed Parts2Whole 114 framework described herein) achieved promising results on all five-target tasks across organs, diseases, datasets, and modalities. Specifically, for NCC 102 and LCS 104, the disclosed Parts2Whole 114 framework not only has higher AUC 107/IoU 108 scores and lower standard deviations but also significantly outperforms Models Genesis 113 based on the t-test ($p<0.05$).

Conversely, Models Genesis 113 achieves better performance by a small margin on NCS 103 and FCC 105 tasks. On the BMS task (far right column of Table 1), which has considerable distance from the proxy dataset (e.g., utilizing different disease, organ, and modality), the disclosed Parts2Whole 114 framework is still competitive compared to other baselines. Furthermore, the disclosed Parts2Whole 114 framework saves about 23% of the proxy task training time compared with Models Genesis 113 (e.g., refer to FIGS. 6A, 6B, and 6C for additional detail), suggesting the disclosed Parts2Whole 114 framework is more efficient. Further still, because Models Genesis 113 provides both a pre-trained encoder and decoder, it would be expected to have certain advantages on segmentation tasks such as NCS 103, LCS 104, and BMS 106. Nonetheless, the disclosed Parts2Whole 114 framework yields promising results on all segmentation tasks with the same architecture (e.g., 3D U-Net) and a randomly initialized decoder, suggesting the encoder pre-trained with the disclosed Parts2Whole 114 framework learns features with strong transferability.

An experimental investigation of the properties of feature representations learned in Parts2Whole is discussed in greater detail below.

Figure 2A:
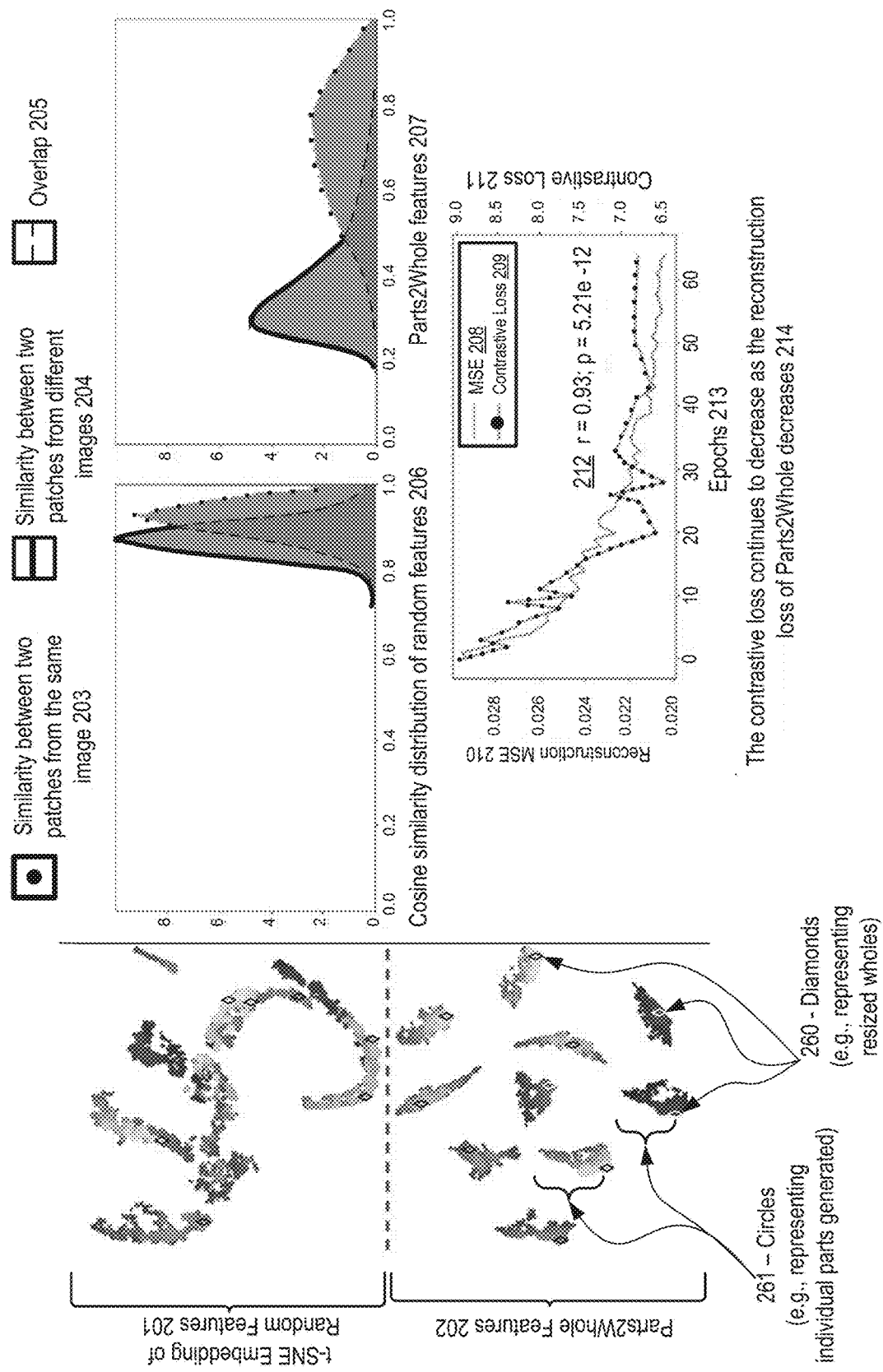
FIG. 2A depicts visualizations of t-SNE embeddings of random features and Parts2Whole features which are charted to depict the similarities and contrastive loses, in accordance with disclosed embodiments.

FIG. 2A depicts visualizations of t-SNE embeddings of random features 201 and Parts2Whole features 202 which are then charted to depict the similarities and contrastive losses.

More particularly, the t-SNE embeddings of random and Parts2Whole features 201 and the Parts2Whole features 202 are charted at the top right to show the cosine similarity of random features 206 and the Parts2Whole features 207, where the dotted line represents the similarity between the two patches from the same image 203, where the solid line represents the similarity between two patches from different images 205 and further in which the dashed line represents the overlap 205. Lastly, at the bottom right, the contrastive loss is shown to continue to decrease as the reconstruction loss of Parts2Whole decreases 214, with the vertical axis showing the reconstructive MSE 210 on the left and the contrastive loss 211 on the right and further in which the horizontal axis depicts the results charted against epochs 213.

The t-SNE embeddings of random and Parts2Whole features 201 were visualized so as to aid in understanding the learned representations. In the example depicted here, ten images were randomly selected and then 200 parts were generated from each image.

Within the t-SNE embeddings of random and Parts2Whole features 201 and the Parts2Whole features 202 depicted at the left-most side, each circle 261 represents the individual parts generated whereas the diamonds 260 represent the resized wholes. The various sizes and degree of shading of the individual circles 261 denote the different images and crop scales for each of the entangled random features 201 and the Parts2Whole features 202, as depicted on the left most side of FIG. 2A. Unlike the entangled random features 201, the Parts2Whole features 202 from the same images are well grouped, while features from different images are highly separatable. As further depicted via the upper right charts of FIG. 2A, the entire validation set was leveraged and the cosine similarity 206 was measured between features of two parts belonging to the same or different images. Notably, the distributions of Parts2Whole features 207 are more separable than those of random features 206, indicating that Parts2Whole learns better representations.

As further depicted at the bottom right chart of FIG. 2A, the contrastive loss is demonstrated to continue to decrease as the reconstruction loss decreases (refer to element 214), thus validating that the described Parts2Whole framework does indeed learn contrastive representations.

Parts2Whole learns contrastive representations. According to a particular embodiment, so as to understand the feature representations learned with the described Parts2Whole framework, the t-SNE embeddings of random features 202 and Parts2Whole features 201 were visualized by randomly selecting 10 whole images and then generating 200 parts for each image with a crop scale [1/16, 1]. As noted previously, each circle 261 represents by one part (generated) while each diamond 260 represents a resized whole image (for instance, with a cropping scale equal to one (1)) and the different shades and circle sizes denote different images and crop scales.

Unlike the entangled features from random initialization, the Parts2Whole features (see elements 202 and 207) are very discriminative for different images. That is to say, features from the same images are well grouped, while those from different images are highly separable. More importantly, although the network is never trained with large patches or the whole image (e.g., crop scale equal to [1/4, 1]), it still correctly aligns the features of small and large patches from the same image together.

This impressive generalization ability suggests that the described Parts2Whole framework learns feature representations that embed the part-whole semantics. To further analyze the feature representations, all of the validation images were leveraged, such that for each image $x_i$, 100 pairs of parts were generated from it (referred to as positive pairs). Additionally, 100 negative pairs were generated, while each one contains one part from $x_i$ and one part from another image. The cosine similarity 206 was calculated between each positive/negative pair. The similarity distributions of random features 201 and Parts2Whole features 202 are those depicted at the left most portion of FIG. 2A, demonstrating that the distributions of Parts2Whole features 202 are more separable than those of random features 201, and further indicating that Parts2Whole learns contrastive features.

Further investigated was the change of the contrastive loss along the training process which is depicted at the lower right chart of FIG. 2A, in which every whole image was tested 100 times, while in each test, one (1) positive pair was randomly generated and 5000 negative pairs were randomly generated for the contrastive loss calculation. As illustrated, the contrastive loss continues to decrease as the reconstruction loss decreases (element 214). Further still, the Pearson product-moment correlation analysis was performed between the reconstruction loss and the contrastive loss. The high Pearson's r-values were calculated to be 0.93 with a p-value of 5.21e-12 (refer to element 213 at the lower right chart), indicating a strong positive correlation, effectively validating that Parts2Whole minimizes the contrastive losses and learns contrastive representations with an image reconstruction framework.

Finally, the relationship between the reconstruction loss in the proxy task and the test performance in target tasks was systematically investigated (refer again to FIGS. 6C and 6D for additional detail). The results indicate that the superior target performance is attributable to the decreasing of reconstruction loss and the learned contrastive features.

FIG. 29 depicts Table 2 at element 299 describing the target task performance on source models pre-trained on different proxy task settings.

By removing skip connections (comparing column 2 at element 252 depicting a crop scale of [1/16, 1] with skip connections with column 3 at element 253 depicting a crop scale of [1/16, 1]) without skip connections, the target performance improves significantly by 5.30 and 2.08 points in NCC 258 and NCS 259, respectively, suggesting that skip connections provide some shortcuts to solve the proxy task using lower-level details. Further, it may be observed here that by modifying the settings 251 and reducing the cropping scale from column 3 at element 253 having a crop scale of [1/16, 1]) to column 4 at element 254 having a crop scale of [1/16, 1/2]) to column 5 at element 255 having a crop scale of [1/16, 1/4]) all the way through to the second to last column, which corresponds to column 6 at element 256 having a crop scale of [1/16, 1/8]), the overall performer continuously increases, and then plateaus 261 at a crop scale of [1/16, 1/4], and appears to saturate when the crop scale is less than 1/8.

Conversely, when the parts are too small, such as when the crop scale is [1/32, 1/16]) as is depicted at the last and right-most column, corresponding to column 7 at element 257, then the score is shown to drop by 3.15 and 0.57 points in NCC 258 and NCS 259, respectively. These observations indicate the importance of part sizes in the disclosed proxy task design.

At Table 2 above, the source model is trained with skip connections ("s.c.") between the encoder and decoder and both pre-trained encoder and decoder were fine-tuned on the target task as indicated by element 260 pointing to the non-bolded outlined boxed results.

Ablation Study: A good proxy task needs to be hard but feasible. The Parts2Whole framework and design as described herein thus configures and customizes two notable components, specifically, the intentional removal of skip connections and further the selecting proper part sizes. The impacts of the two components were ablated to justify the described proxy task design. Source models pre-trained with different proxy task settings on NCC 258 and NCS 259 target tasks with 45% and 10% training data were evaluated, with the experimental results set forth at Table 2, as discussed above.

The effects of skip connections were first studied as shown at Columns 2 (at element 252) through column 3 (at element 253). By removing skip connections while keeping the same cropping scale, the target performance improves significantly by 5.30 and 2.08 points in NCC and NCS, respectively. These results suggest that skip connections may pass lower-level details from the encoder to decoder, and in so doing, provide some shortcuts to solve the proxy task. The same network architecture (i.e., no skip connections) was further studied to determine the effects of different part sizes as shown at Columns 3-7 of Table 2. When the upper bound of part sizes is gradually reduced, the overall performer continuously increases, plateaus at 1/4, and appears to saturate at 1/8. Conversely, when the parts are too small (i.e., less than 1/16), the target performance drops by 3.15 and 0.57 points in NCC and NCS, respectively. These observations indicate the importance of proper part sizes as specially configured for the disclosed proxy task design, in which the parts should be small enough to avoid trivial solutions while large enough to contain enough information to recover the whole images. In other words, the idea that a good proxy task should be hard enough but still feasible is validated by the results shown here.

Parts2Whole 2D offers performance on par with Models Genesis 2D: While the preferred focus is on 3D imaging, the power of the described Parts2Whole framework was further evaluated for 2D applications by utilizing the ChestX-ray 14 dataset and compared with Models Genesis 2D. For the evaluation, 14 diseases were classified utilizing the official split, which are different from the DXC task. A 2D model, which may be referred to as Parts2Whole 2D framework, was pre-trained, on the training split. The Parts2Whole 2D framework as described herein achieved 79.95±0.19 AUC scores, providing performance on par with Models Genesis 2D (79.82±0.10) with p>0.1. The same hyper-parameters were utilized (e.g., crop scale) as was deployed in the 3D pre-training without any additional tuning. Therefore, it is expected that performance may be further boosted for 2D image processing by selecting hyper-parameters which are specifically tailored for 2D image processing.

It is therefore in accordance with the described embodiments that a new self-supervised framework, Parts2Whole, is provided which directly exploits the universal and intrinsic part-whole relationship. The disclosed Parts2Whole framework demonstrably learns contrastive representations in an image reconstruction framework. The experimental results show that the resulting pre-trained model achieves competitive performance over four publicly available pre-trained 3D models on five distinct medical target tasks.

Because only the part-whole relationship was used, incorporating other domain knowledge or transformations are expected to further improve results. For instance, alternative embodiments specifically include color/intensity transformations since the similar intensity distribution across parts from one image may provide shortcuts to solve the proxy task.

Figure 3:
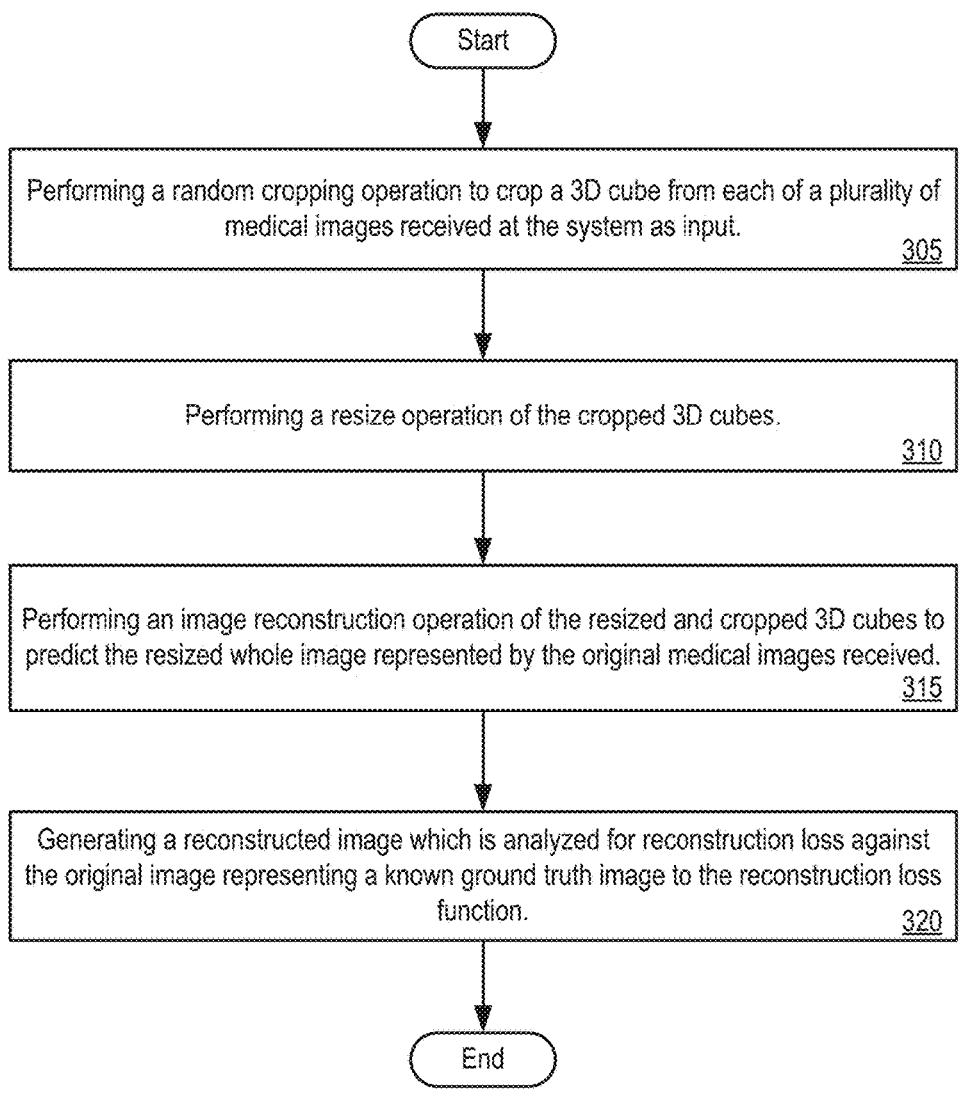
FIG. 3 depicts a flow diagram illustrating a method for training a deep model to learn contrastive representations embedded within part-whole semantics via a self-supervised learning framework, in accordance with disclosed embodiments.

FIG. 3 depicts a flow diagram illustrating a method 300 for training a deep model to learn contrastive representations embedded within part-whole semantics via a self-supervised learning framework, in which the trained deep models are then utilized for the processing of medical imaging, in accordance with disclosed embodiments. Method 300 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 401 (see FIG. 4) and the machine 501 (see FIG. 5) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to method 300 depicted at FIG. 3, there is a method performed by a system specially configured for the training a deep model to learn contrastive representations embedded within part-whole semantics via a self-supervised learning framework in the absence of manual labeling of 3D medical imagery.

Such a system may be configured with at least a processor and a memory to execute specialized instructions which cause the system to perform the following operations:

At block 305, processing logic performs a random cropping operation to crop a 3D cube from each of a plurality of medical images received at the system as input.

At block 310, processing logic performs a resize operation of the cropped 3D cubes.

At block 315, processing logic performs an image reconstruction operation of the resized and cropped 3D cubes to predict the resized whole image represented by the original medical images received.

At block 320, processing logic generates a reconstructed image which is analyzed for reconstruction loss against the original image representing a known ground truth image to the reconstruction loss function.

According to another embodiment of method 300, randomly cropping the 3D cube comprises cropping the 3D cube utilizing random scales and random aspect ratios.

According to another embodiment of method 300, the random scales and random aspect ratios utilized for the random cropping erase low-level cues across different parts but maintain informative structures and textures amongst the randomly cropped 3D cubes.

According to another embodiment of method 300, resizing the cropped 3D cubes comprises resizing the cropped 3D cubes to produce transformed part for later reconstruction.

According to another embodiment of method 300, the reconstruction is to predict the resized whole image from a local patch by training an encoder-decoder pair to minimize the loss function between the transformed part produced via the random cropping and resizing and the original whole image.

According to another embodiment of method 300, the encoder learns contrastive representations that embed the part-whole semantics.

According to another embodiment of method 300, all skip connections connecting the encoder and decoder are removed from a U-Net architecture.

According to another embodiment of method 300, the skip connections remain absent during training so as to force the bottleneck representations encoding high-level information.

According to another embodiment of method 300, a part size via which to resize the cropped 3D cube is configurable to avoid training an auto encoder without learning semantics when the part size is too large and to avoid an unsolvable task when the part size is too small so as to lack sufficient information.

According to a particular embodiment, there is a non-transitory computer-readable storage medium having instructions stored thereupon that, when executed by a system having at least a processor and a memory therein, the instructions cause the system to perform operations including: performing a random cropping operation to crop a 3D cube from each of a plurality of medical images received at the system as input; performing a resize operation of the cropped 3D cubes; performing an image reconstruction operation of the resized and cropped 3D cubes to predict the resized whole image represented by the original medical images received; and generating a reconstructed image which is analyzed for reconstruction loss against the original image representing a known ground truth image to the reconstruction loss function.

Figure 4:
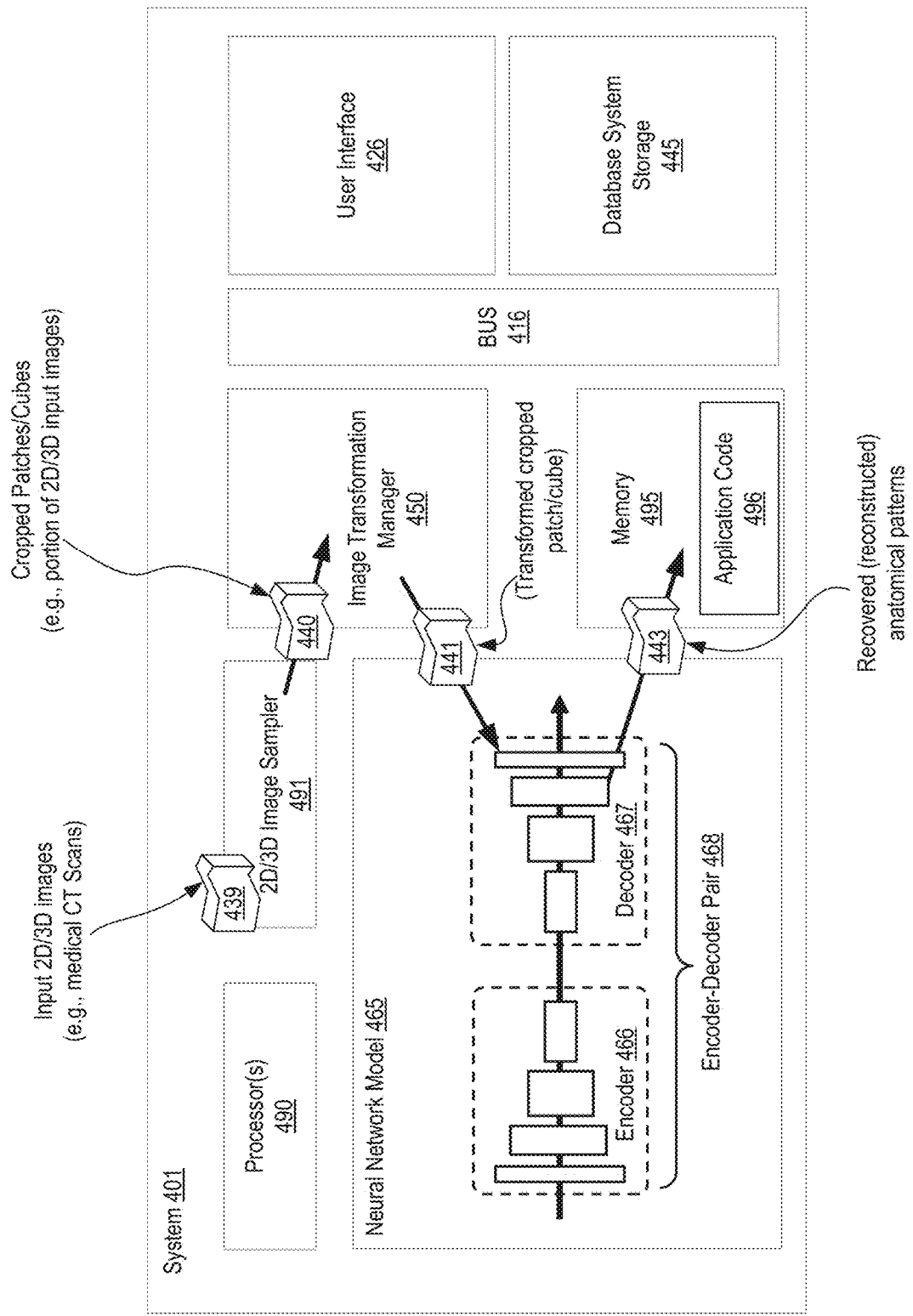
FIG. 4 shows a diagrammatic representation of a system within which embodiments may operate, be installed, integrated, or configured, in accordance with disclosed embodiments.

FIG. 4 shows a diagrammatic representation of a system 401 within which embodiments may operate, be installed, integrated, or configured. In accordance with one embodiment, there is a system 401 having at least a processor 490 and a memory 495 therein to execute implementing application code 496. Such a system 401 may communicatively interface with acid cooperatively execute with the benefit of remote systems, such as a user device sending instructions and data, a user device to receive as an output from the system 401.

According to the depicted embodiment, the system 401, includes the processor 490 and the memory 495 to execute instructions at the system 401. The system 401 as depicted here is specifically customized and configured specifically to train a deep model (e.g., the neural network model 465 having the encoder 466 and decoder 467 (e.g., an encoder-decoder pair 468) embodied therein) to learn contrastive representations embedded within part-whole semantics via a self supervised learning framework in the absence of manual labeling of 3D medical imagery, in accordance with disclosed embodiments.

According to a particular embodiment, system 401 is further configured to execute instructions via the processor for performing a random cropping operation to crop a 3D cube 440 from each of a plurality of medical images received 439 at the system as input. The cropping may be performed by the image transformation manager 450. Such a system is further configured to execute instructions via the processor 490 for performing a resize operation of the cropped 3D cubes, resulting in the transformed 441 cropped (and now resized) patches or cubes from a 2D or 3D image respectively. The image resizing may also be performed by the image transformation manager 450. The system is further configured to execute instructions via the processor 490 for performing an image reconstruction operation of the resized and cropped 3D cubes to predict the resized whole image represented by the original medical images received. The system is further configured to generating a reconstructed image 443 which is analyzed for reconstruction loss against the original image representing a known ground truth image to the reconstruction loss function.

The model output manager 485 may further transmit output back to a user device or other requestor, for example, via the user interface 426, or such information may alternatively be stored within the database system storage 445 of the system 401.

According to another embodiment of the system 401, a user interface 426 communicably interfaces with a user client device remote from the system and communicatively interfaces with the system via a public Internet.

Bus 416 interfaces the various components of the system 401 amongst each other, with any other peripheral(s) of the system 401, and with external components such as external network elements, other machines, client devices, cloud computing services, etc. Communications may further include communicating with external devices via a network interface over a LAN, WAN, or the public Internet.

Figure 5:
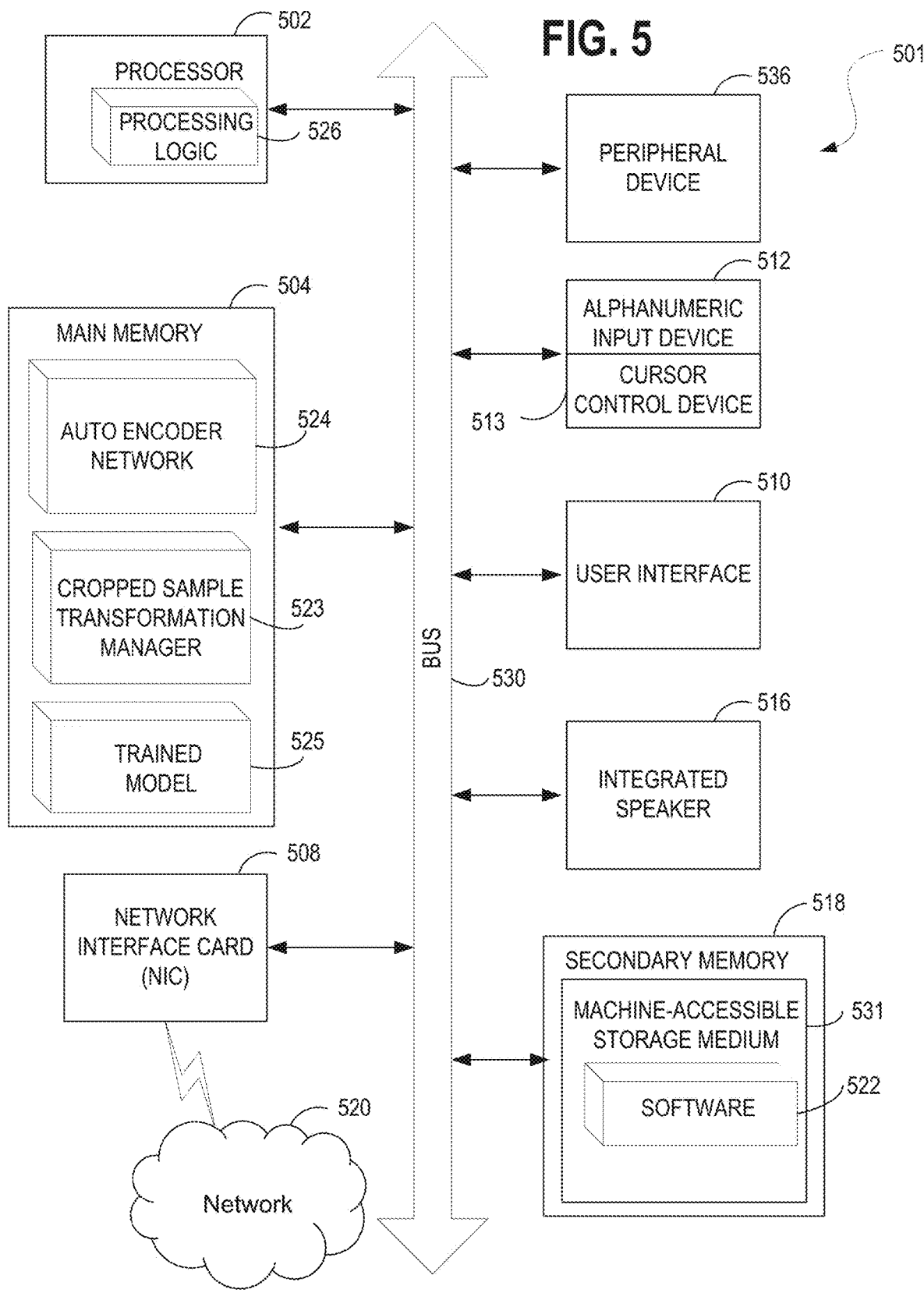
FIG. 5 illustrates a diagrammatic representation of a machine in the exemplary form of a computer system, in accordance with one embodiment.

FIG. 5 illustrates a diagrammatic representation of a machine 501 in the exemplary form of a computer system, in accordance with one embodiment, within which a set of instructions, for causing the machine/computer system 501 to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 501 includes a processor 502, a main memory 504 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 518 (e.g., a persistent storage device including hard disk drives and a persistent database and/or a multi-tenant database implementation), which communicate with each other via a bus 530. Main memory 504 includes an auto encoder network 524 (e.g., such as an encoder-decoder implemented via a neural network model but without skip connections) for performing self-learning operations on randomly cropped and resized samples as provided via the cropped sample transformation manager 523, so as to train a deep model to learn contrastive representations embedded within part-whole semantics via a self-supervised learning framework in the absence of manual labeling of 3D medical imagery resulting in the trained model 525 in support of the methodologies and techniques described herein. Main memory 504 and its sub-elements are further operable in conjunction with processing logic 526 and processor 502 to perform the methodologies discussed herein.

Processor 502 represents one or more specialized and specifically configured processing devices such as a microprocessor, central processing unit, or the like. More particularly, the processor 502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 502 may also be one or more special-purpose processing devices such as an application-specific integrated circuit (ASIC), a field programmable gate array (FPGA), a digital signal processor (DSP), network processor, or the like. Processor 502 is configured to execute the processing logic 526 for performing the operations and functionality which is discussed herein.

The computer system 501 may further include a network interface card 508. The computer system 501 also may include a user interface 510 (such as a video display unit, a liquid crystal display, etc.), an alphanumeric input device 512 (e.g., a keyboard), a cursor control device 513 (e.g., a mouse), and a signal generation device 516 (e.g., an integrated speaker). The computer system 501 may further include peripheral device 536 (e.g., wireless or wired communication devices, memory devices, storage devices, audio processing devices, video processing devices, etc.).

The secondary memory 518 may include a non-transitory machine-readable storage medium or a non-transitory computer readable storage medium or a non-transitory machine-accessible storage medium 531 on which is stored one or more sets of instructions (e.g., software 522) embodying any one or more of the methodologies or functions described herein. The software 522 may also reside, completely or at least partially, within the main memory 504 and/or within the processor 502 during execution thereof by the computer system 501, the main memory 504 and the processor 502 also constituting machine-readable storage media. The software 522 may further be transmitted or received over a network 520 via the network interface card 508.

Figure 6A:
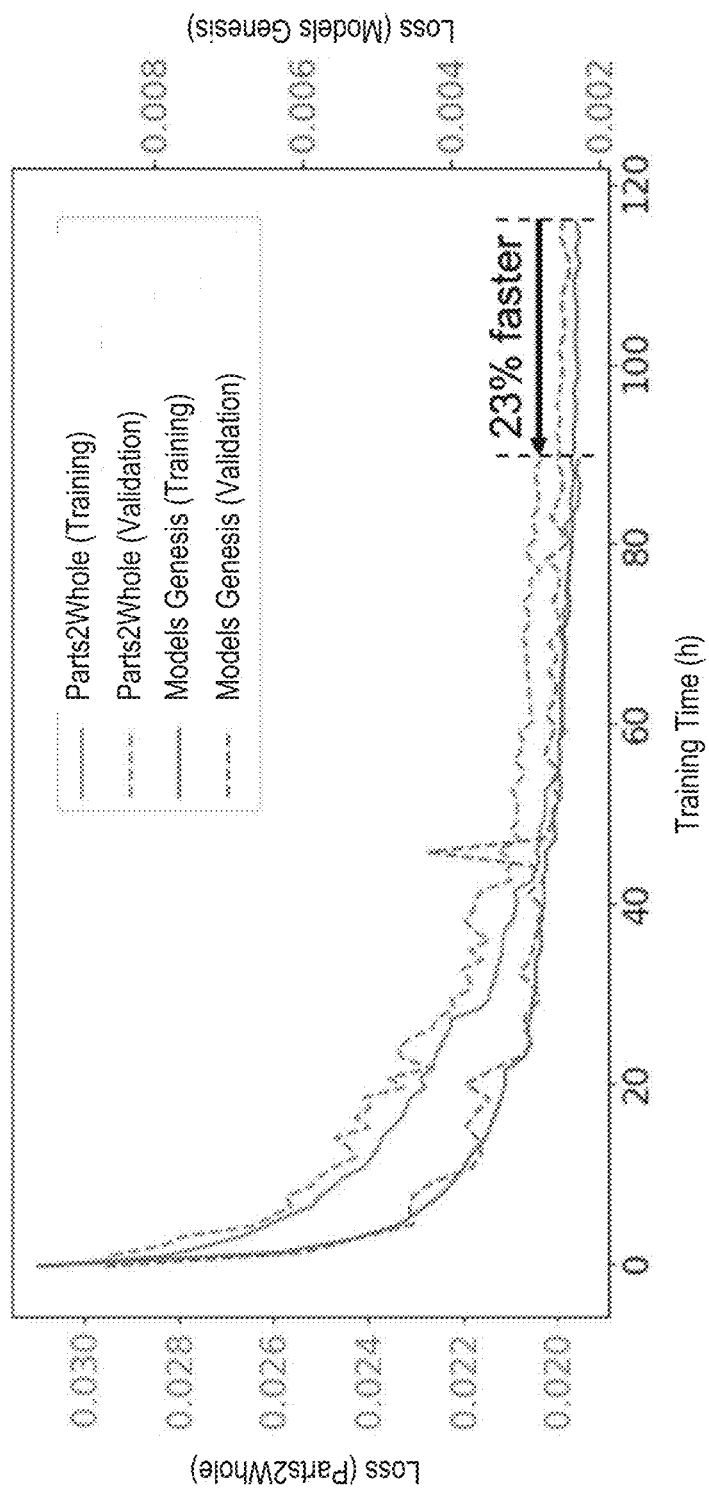
FIG. 6A depicts the use of the Parts2Whole framework which saves 23% proxy task training time compared with Models Genesis while maintaining very competitive performance across five (5) distinctive target tasks, in accordance with disclosed embodiments.

FIG. 6A depicts the use of the Parts2Whole framework which saves 23% proxy task training time compared with Models Genesis while maintaining very competitive performance across five (5) distinctive target tasks.

FIG. 6B depicts Table 3 at element 699 describing how the Parts2Whole framework makes contrastive representation learning feasible for 3D medical imaging.

As an example, InsDisc requires a memory bank with approximately ~28 GB of storage capacity within which to persistently store feature representations of all images in the training set, exceeding GPU memory of Titan XP, thus making InsDisc infeasible from a practical standpoint to utilize the full training set due to hardware limitations. Therefore, the training set size was reduced to 5,000 and then training was performed using both InsDisc and the Parts2Whole framework as described herein. As shown by the results of Table 3, by learning contrastive representations in an image reconstruction framework, the disclosed Parts2Whole framework outperforms InsDisc by a small margin with a reduced training set, and achieves significantly better performance when training with the full training set. Based on these observations, the disclosed Parts2Whole framework is shown to benefit more by utilizing a larger database, such as LIDC-IDRI and NLST.

Figure 6C:
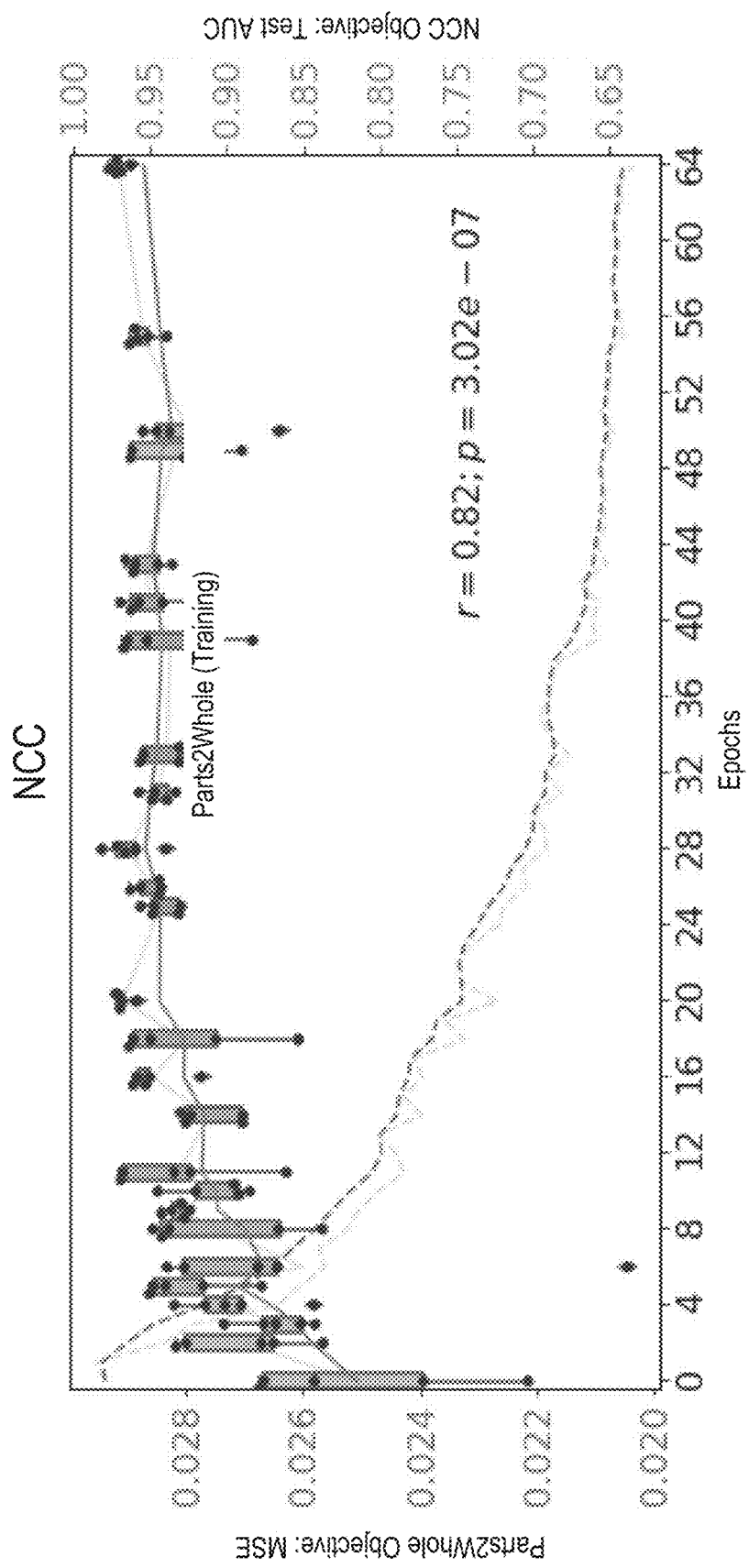
FIGS. 6C and 6D depict that the overall performance of target tasks continues to improve as the validation loss in the proxy task decreases, in accordance with disclosed embodiments.
Figure 6D:
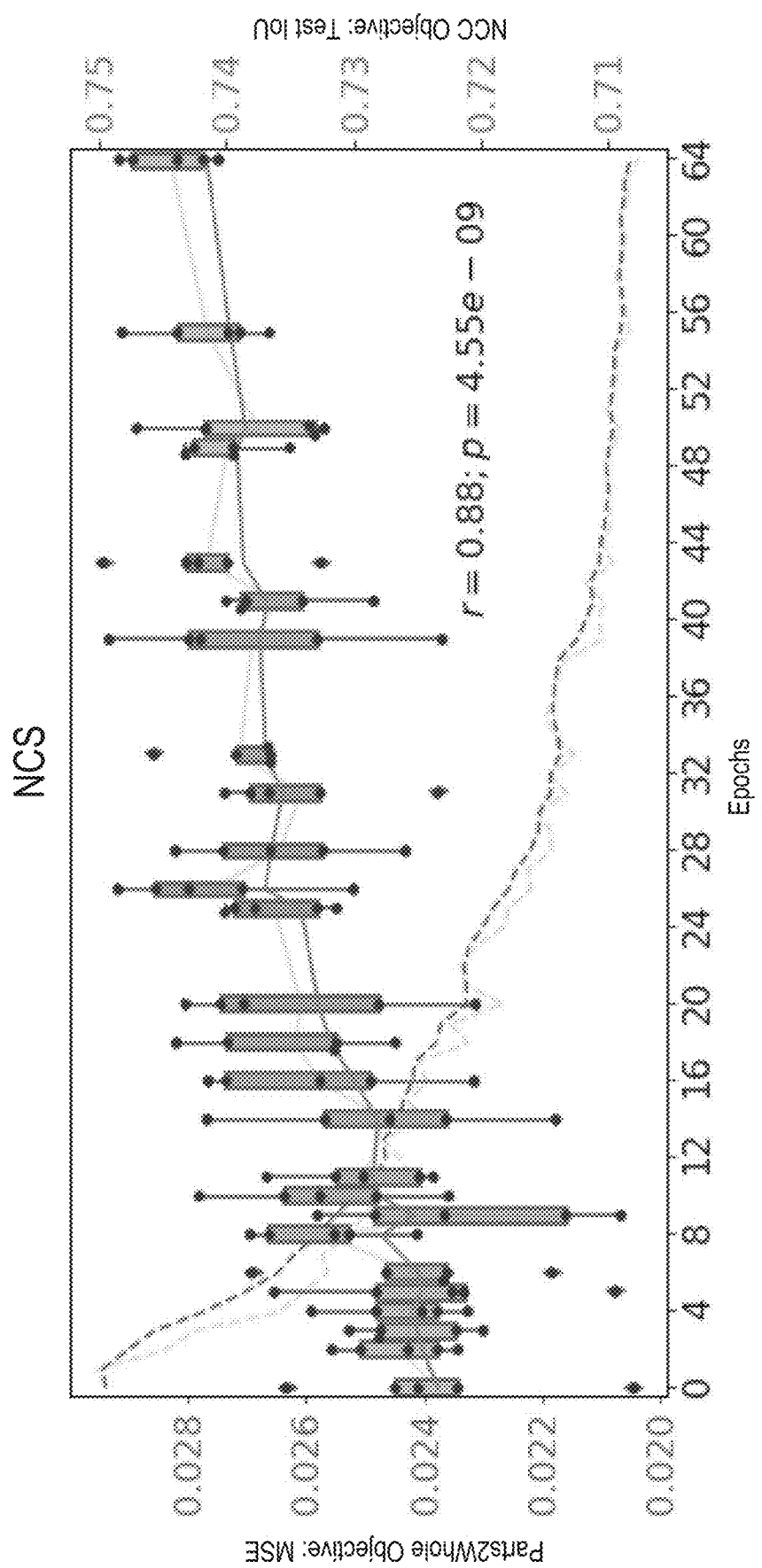

FIGS. 6C and 6D depict that the overall performance of target tasks continues to improve as the validation loss in the proxy task decreases. A good proxy task is able to improve the target task performance consistently as the proxy objective is optimized. Therefore, the consistency of proxy and task objectives is validated by evaluating twenty-six (26) checkpoints saved in the proxy training process. Specifically, every checkpoint is iteratively fine-tuned five (5) times on both NCC and NCS target tasks. So as to reduce the computational cost, only use partial training data is utilized (e.g., 45% for NCC and 10% NCS). The amount of training data is selected such that the fine-tuning performance of the last checkpoint (e.g., the final model) is not lower than training from scratch.

From the NCC and NCS charts depicted at FIGS. 6C and 6D, it is clear that as the proxy loss decreases, the average AUC/IoU score increases while the standard deviation decreases, suggesting that the pre-trained model becomes more generic and robust. Additionally, the Pearson product-moment correlation analysis is performed between the proxy objective (e.g., reconstruction quality, measured by (1-MSE)) and target objective (measured by AUC/IoU score). Although the target tasks include both classification and segmentation operations, the experimental results indicate a strong positive co-relationship between proxy and target objectives (e.g., with a Pearson's r-value>0.5). It also suggests that target performance may be further improved by better optimizing the proxy task training process.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:
a memory to store instructions;
a processor to execute the instructions stored in the memory;
wherein the system is specially configured to learn contrastive representations embedded within part-whole semantics via a self-supervised learning framework, by performing the following operations:
performing a random cropping operation to crop a 3D cube from each of a plurality of medical images received at the system as input;
performing a resize operation of the cropped 3D cubes;
performing an image reconstruction operation of the resized and cropped 3D cubes to predict the resized whole image represented by the original medical images received; and
generating a reconstructed image which is analyzed for reconstruction loss against the original image representing a known ground truth image to the reconstruction loss function.

2. The system of claim 1, wherein randomly cropping the 3D cube comprises cropping the 3D cube utilizing random scales and random aspect ratios.

3. The system of claim 2, wherein the random scales and random aspect ratios utilized for the random cropping erase low-level cues across different parts but maintain informative structures and textures amongst the randomly cropped 3D cubes.

4. The system of claim 1, wherein resizing the cropped 3D cubes comprises resizing the cropped 3D cubes to produce transformed part for later reconstruction.

5. The system of claim 1, wherein the reconstruction is to predict the resized whole image from a local patch by training an encoder-decoder pair to minimize the loss function between the transformed part produced via the random cropping and resizing and the original whole image.

6. The system of claim 5, wherein the encoder learns contrastive representations that embed the part-whole semantics.

7. The system of claim 5, wherein all skip connections connecting the encoder and decoder are removed from a U-Net architecture.

8. The system of claim 7, wherein the skip connections remain absent during training so as to force a bottleneck representation encoding high-level information.

9. The system of claim 1, wherein a part size via which to resize the cropped 3D cube is configurable to avoid training an auto encoder without learning semantics when the part size is too large and to avoid an unsolvable task when the part size is too small so as to lack sufficient information.

10. Non-transitory computer-readable storage media having instructions stored thereupon that, when executed by a system having at least a processor and a memory therein, the instructions cause the system to learn contrastive representations embedded within part-whole semantics via a self-supervised learning framework, by performing operations including:
performing a random cropping operation to crop a 3D cube from each of a plurality of medical images received at the system as input;
performing a resize operation of the cropped 3D cubes;
performing an image reconstruction operation of the resized and cropped 3D cubes to predict the resized whole image represented by the original medical images received; and generating a reconstructed image which is analyzed for reconstruction loss against the original image representing a known ground truth image to the reconstruction loss function.

11. The non-transitory computer readable storage media of claim 10:
wherein randomly cropping the 3D cube comprises cropping the 3D cube utilizing random scales and random aspect ratios; and
wherein the random scales and random aspect ratios utilized for the random cropping erase low-level cues across different parts but maintain informative structures and textures amongst the randomly cropped 3D cubes.

12. The non-transitory computer readable storage media of claim 10:
wherein resizing the cropped 3D cubes comprises resizing the cropped 3D cubes to produce transformed part for later reconstruction.

13. The non-transitory computer readable storage media of claim 10:
wherein the reconstruction is to predict the resized whole image from a local patch by training an encoder-decoder pair to minimize the loss function between the transformed part produced via the random cropping and resizing and the original whole image.

14. The non-transitory computer readable storage media of claim 13:
wherein the encoder learns contrastive representations that embed the part-whole semantics.

15. The non-transitory computer readable storage media of claim 13:
wherein all skip connections connecting the encoder and decoder are removed from a U-Net architecture; and
wherein the skip connections remain absent during training so as to force a bottleneck representation encoding high-level information.

16. The non-transitory computer readable storage media of claim 10:
wherein a part size via which to resize the cropped 3D cube is configurable to avoid training an auto encoder without learning semantics when the part size is too large and to avoid an unsolvable task when the part size is too small so as to lack sufficient information.

17. A method performed by a system having at least a processor and a memory therein to execute instructions for learning contrastive representations embedded within part-whole semantics via a self-supervised learning framework, wherein the method comprises:
performing a random cropping operation to crop a 3D cube from each of a plurality of medical images received at the system as input;
performing a resize operation of the cropped 3D cubes;
performing an image reconstruction operation of the resized and cropped 3D cubes to predict the resized whole image represented by the original medical images received; and
generating a reconstructed image which is analyzed for reconstruction loss against the original image representing a known ground truth image to the reconstruction loss function.

18. The method of claim 17:
wherein randomly cropping the 3D cube comprises cropping the 3D cube utilizing random scales and random aspect ratios; and
wherein the random scales and random aspect ratios utilized for the random cropping erase low-level cues across different parts but maintain informative structures and textures amongst the randomly cropped 3D cubes.

19. The method of claim 17:
wherein the reconstruction is to predict the resized whole image from a local patch by training an encoder-decoder pair to minimize the loss function between the transformed part produced via the random cropping and resizing and the original whole image.

20. The method of claim 19: wherein all skip connections connecting the encoder and decoder are removed from a U-Net architecture; and wherein the skip connections remain absent during training so as to force a bottleneck representation encoding high-level information.

* * * * *